United States Patent
Heinnickel et al.

(10) Patent No.: US 12,115,492 B2
(45) Date of Patent: Oct. 15, 2024

(54) PHOTOTROPHIC PURIFICATION OF HYDROGEN SULFIDE CONTAINING STREAMS

(71) Applicant: ExxonMobil Technology and Engineering Company, Annandale, NJ (US)

(72) Inventors: Mark L Heinnickel, Maplewood, NJ (US); Steven W Levine, Hopewell, NJ (US); Robert D Nielsen, Lambertville, NJ (US); Yuchen Liu, Annandale, NJ (US); Joseph C Weissman, High Bridge, NJ (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 890 days.

(21) Appl. No.: 17/082,166

(22) Filed: Oct. 28, 2020

(65) Prior Publication Data

US 2021/0220770 A1    Jul. 22, 2021

Related U.S. Application Data

(60) Provisional application No. 62/963,262, filed on Jan. 20, 2020.

(51) Int. Cl.

| | |
|---|---|
| *B01D 53/14* | (2006.01) |
| *B01D 53/52* | (2006.01) |
| *B01D 53/96* | (2006.01) |
| *C01C 1/02* | (2006.01) |
| *C01C 1/04* | (2006.01) |
| *C12M 1/00* | (2006.01) |
| *C12N 9/10* | (2006.01) |
| *C12P 3/00* | (2006.01) |
| *C12P 7/64* | (2022.01) |
| *C12P 13/00* | (2006.01) |
| *C12P 19/04* | (2006.01) |

(52) U.S. Cl.
CPC ..... *B01D 53/1425* (2013.01); *B01D 53/1468* (2013.01); *B01D 53/1493* (2013.01); *B01D 53/52* (2013.01); *B01D 53/96* (2013.01); *C01C 1/026* (2013.01); *C01C 1/04* (2013.01); *C12M 21/02* (2013.01); *C12N 9/1085* (2013.01); *C12Y 205/01* (2013.01); *B01D 2251/90* (2013.01); *B01D 2251/95* (2013.01); *B01D 2257/304* (2013.01); *C12P 3/00* (2013.01); *C12P 7/64* (2013.01); *C12P 13/005* (2013.01); *C12P 19/04* (2013.01)

(58) Field of Classification Search
CPC .. B01D 53/526; B01D 53/1493; B01D 53/52; B01D 53/1425; B01D 53/1468; B01D 53/96; B01D 2257/304; B01D 2251/902; B01D 2251/95; B01D 2251/00; B01D 2251/90; B01D 2256/24; B01D 2251/904; C01C 1/026; C01C 1/04; C12Y 205/01; C12N 9/1085; C12M 31/10; C12M 21/02; Y02E 50/30; C12P 13/005; C12P 7/64; C12P 19/04; C12P 3/00
See application file for complete search history.

(56) References Cited

U.S. PATENT DOCUMENTS

| | | | |
|---|---|---|---|
| 4,382,918 A | 5/1983 | Diaz | |
| 4,666,852 A | 5/1987 | Cork | |
| 5,126,118 A | 6/1992 | Hardison | |
| 6,083,472 A * | 7/2000 | Nagl | C01B 17/05 423/576.5 |
| 2013/0344400 A1 | 12/2013 | Girguis et al. | |
| 2017/0175152 A1 | 6/2017 | McNeely et al. | |

FOREIGN PATENT DOCUMENTS

| | | | | |
|---|---|---|---|---|
| CN | 206366311 U | 8/2017 | | |
| WO | WO-2020214843 A1 * | 10/2020 | | A01C 1/06 |

OTHER PUBLICATIONS

Ball et al. Oxidation of hydrogen sulphide in sour gas by Chlorobium limicola. Enzyme and Microbial Technology (2007), 41, 702-705. (Year: 2007).*
Maat et al. The removal of hydrogen sulfide from gas streams using an aqueous metal sulfate absorbent Part I. The absorption of hydrogen sulfide in metal sulfate solutions. Separation and Purification Technology 43 (2005) 183-19. (Year: 2005).*
K.E. Shuman Metabolic and Regulatory Properties of Sulfide Oxidation in Chlorobaculum Tepidum. PhD Dissertation, Winter 2016. (Year: 2016).*

* cited by examiner

*Primary Examiner* — Sean C. Barron
(74) *Attorney, Agent, or Firm* — Shook, Hardy & Bacon L.L.P.

(57) ABSTRACT

The present disclosure relates to processes for desulfurizing hydrocarbon feedstocks. The processes may include introducing a feedstock comprising hydrogen sulfide to an absorber comprising a metal chelate to form a reduced metal chelate. The processes may further include introducing the reduced metal chelate to a photobioreactor comprising a phototrophic bacterium. The present disclosure also relates to apparatuses for desulfurizing hydrocarbon feedstock. An apparatus may include and absorber and a photobioreactor fluidly connected to the absorber. The photobioreactor may be an anaerobic vessel with a light source.

17 Claims, 1 Drawing Sheet
Specification includes a Sequence Listing.

PHOTOTROPHIC PURIFICATION OF HYDROGEN SULFIDE CONTAINING STREAMS

CROSS-REFERENCE TO RELATED APPLICATIONS

This application claims the benefit of priority from U.S. Provisional Application No. 62/963,262 filed Jan. 20, 2020, which is herein incorporated by reference in its entirety.

REFERENCE TO A SEQUENCE LISTING

This application contains references to amino acid sequences and/or nucleic acid sequences which have been submitted as the sequence listing text file entitled "2020EM010-US2-SequenceListing.txt", file size 11 Kilo-Bytes (KB), created 15 Dec. 2020, which is herein incorporated by reference in its entirety.

FIELD OF THE INVENTION

The present disclosure relates to the use of genetically modified bacteria to purify hydrocarbon streams.

BACKGROUND OF THE INVENTION

Sulfur content in hydrocarbons may hinder the performance of catalyst systems in reformation catalysts, hydroprocessing (including hydrotreating, hydrocracking and hydroisomerization), catalytic converters, fluidized bed reactors, and internal combustion engines. Additionally, the sulfur content of hydrocarbon fuels is subject to strict regulations. Therefore, sulfur in hydrocarbons is typically reduced or eliminated in the oil & gas industry.

In refineries, sulfur is reduced in distillate fractions by hydrotreating, a process that converts the sulfur in hydrocarbons into hydrogen sulfide ($H_2S$), a flammable gas. The $H_2S$ is then converted to elemental sulfur through the Claus process. In the Claus process, about ⅓ of the $H_2S$ is oxidized to sulfur dioxide, and then the oxidized fraction is used to react with the remaining $H_2S$ to produce elemental sulfur. Although the Claus process is considered the gold standard in sulfur treatment, the high capital cost associated with a Claus plant prevents its implementation in many smaller scale operations, such as sour gas fields. In natural gas, $H_2S$ is commonly (but not always) entrained in hydrocarbon streams extracted from a well. According to certain regulations, $H_2S$ levels have to be reduced to 4 ppm for the gas to enter transportation pipes or be sold for use.

Other sulfur reduction processes have been developed which rely on the redox potential of transition metals for the oxidation of $H_2S$ to elemental sulfur. In redox processes the metal element is reduced while the $H_2S$ is oxidized and the metal is regenerated in a separate redox reaction where oxygen is used to regenerate the metal (via oxidation). The use of transition metal redox reactants typically includes metal chelators, which decompose over time in the presence of oxygen. The constant need to replenish metal chelators means redox processes may also be expensive.

Previous attempts have been made to use biological organisms to oxidize $H_2S$ from hydrocarbon and natural gas streams. This approach was used with the aerobic bacterium *Thiobacillus*. Although this approach can treat large quantities of $H_2S$, it can also lead to the formation of relatively large amounts of sulfate, which is energy-intensive and costly to remove.

Another concern in production of hydrocarbon fuels is the quantity of carbon dioxide ($CO_2$) that is either included in a hydrocarbon stream or produced as part of the refining processes. The aforementioned processes do not remove the $CO_2$ from the feedstock and do not include carbon fixation.

In some cases, phototrophic bacteria (both green and purple sulfur bacteria) is used to treat $H_2S$. In these examples, the oxidation of $H_2S$ is coupled to the reduction of $CO_2$. However, $H_2S$ is toxic to these species, so the oxidation of $H_2S$ in these species is limited at large concentrations. Additionally, as sulfur bacteria have typically evolved in areas of low light, they tend to saturate at low illumination intensities. This means in high light intensities, where they are expected to be their most productive, a large percentage of the absorbed light is wasted as heat or fluorescence. Due to these loses, conversion of $H_2S$ to elemental sulfur requires an excessive amount of light, leading to an inefficient and expensive process. The combination of energy inefficiency and toxicity of $H_2S$ toward phototrophic bacteria has historically made their use in the oil and gas industry undesirable.

There is a need for a hydrogen sulfide removal processes that can be energy efficient, and used in an area where a Claus plant would be impractical. There is a further need for carbon fixation to reduce, for example, carbon dioxide emissions within refinery processes or natural gas production.

Background references include: U.S. Pat. Nos. 4,382,918; 4,666,852; 5,126,118; US2017/0175152A1; US2013/0344400A1; and CN206366311.

SUMMARY OF THE INVENTION

The present disclosure relates to processes for desulfurizing hydrocarbon feedstocks. The processes may include introducing a feedstock including hydrogen sulfide to an absorber including a metal chelate to form a reduced metal chelate. The processes may further include introducing the reduced metal chelate to a photobioreactor comprising a phototrophic bacterium.

The present disclosure also relates to apparatuses for desulfurizing hydrocarbon feedstock. An apparatus may include and absorber and a photobioreactor fluidly connected to the absorber. The photobioreactor may be an anaerobic vessel with a light source.

BRIEF DESCRIPTION OF THE DRAWINGS

So that the manner in which the above recited features of the disclosure can be understood in detail, a more particular description of the disclosure, briefly summarized above, may be had by reference to implementations, some of which are illustrated in the appended drawings. The appended drawings illustrate only typical implementations of this disclosure and are therefore not to be considered limiting of scope, for the disclosure may admit to other equally effective implementations.

Figure 1:
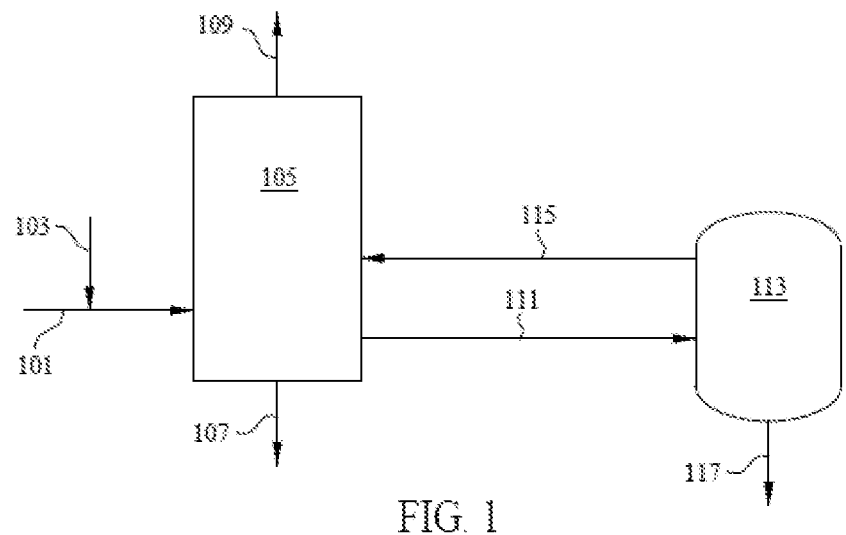
FIG. 1 is an illustration of an apparatus according to an embodiment.

To facilitate understanding, identical reference numerals have been used, where possible, to designate identical elements that are common to the Drawings. It is contemplated that elements and features of one implementation may be beneficially incorporated in other implementations without further recitation.

DETAILED DESCRIPTION OF THE INVENTION

It has been discovered that genetically modified bacteria, such as green-sulfur bacteria, may be coupled with an anaerobic metal redox reaction to remove or reduce hydrogen sulfide from hydrocarbon and natural gas streams. Additionally, processes including genetically modified bacteria may include carbon or nitrogen fixation reducing the amount of CO2 within the hydrocarbon stream and the amount produced in the purification of hydrocarbons. The combination has the potential to lower the cost of hydrogen sulfide treatment while also lowering the carbon emissions associated with a refinery and/or gas treatment processes. Additionally, these approaches may be used when a Claus plant is not feasible due to costs or location.

Definitions

The term "hydrocarbon stream(s)", as employed herein, is intended to include streams containing hydrocarbons, it being recognized that such streams contain "impurities" not technically defined as a hydrocarbon. Streams containing principally a single hydrocarbon, e.g., ethane, or multiple hydrocarbons, may be used as the hydrocarbon stream of the feedstock. Streams derived from the gasification and/or partial oxidation of gaseous or liquid hydrocarbon may be treated.

The term "phototrophic" refers to culture conditions in which light and inorganic carbon (e.g., carbon dioxide, carbonate, bi-carbonate) may be applied to a culture of microorganisms. Microorganisms capable of growing in phototrophic conditions may use light as an energy source and inorganic carbon as a carbon source.

The term "gene," as used herein, may encompass genomic sequences that contain exons, such as polynucleotide sequences capable of encoding polypeptide sequences involved in a specific activity. The term further encompasses synthetic nucleic acids that did not derive from a naturally occurring genomic sequence. In certain embodiments, the genes lack one or more introns of another genomic sequence, as the genes are synthesized based on the known DNA sequence of cDNA and protein sequence. The term can further include nucleic acid molecules including nucleotide sequences having exons and introns.

The term "knockout mutation" or "knockout" refers to a genetic modification that prevents a native gene from being transcribed and translated to produce a functional protein.

Referring to FIG. 1, a feedstock 101 including hydrogen sulfide compounds may have additional fixation gases, such as $CO_2$ and $N_2$ added through line 103 before being introduced to absorber 105. Absorber 105 is designed to allow sulfur compounds, such as hydrogen sulfide ($H_2S$) to come in contact with a chelated metal compound in aqueous solution. Hydrogen sulfide may be oxidized to solid sulfur while the chelated metal compound is reduced. The solid sulfur is removed via line 107. The treated feedstock (that had $H_2S$ removed) may exit the absorber via line 109. The reduced chelated metal compound may be sent for regeneration (oxidation) via line 111 to photobioreactor 113. Photobioreactor 113 is configured to allow for the bacterial oxidation of the chelated metal compound which when regenerated may be recycled to absorber 105 via line 115. Additionally, the combination of absorber and photobioreactor allows for transport of fixation gases to the photobioreactor where the oxidation of the reduced chelated metal compound allows for carbon or nitrogen fixation. Biomass produced may be removed from photobioreactor 113 via line 117.

Figure 2:
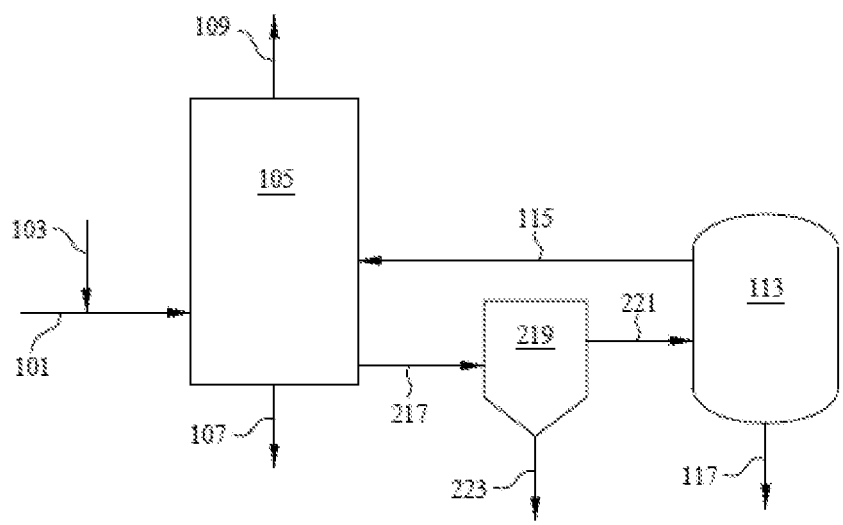
FIG. 2 is an illustration of an apparatus according to an embodiment.

Referring to FIG. 2 feedstock 101 including sulfur compounds may have additional fixation gases added through line 103 before being introduced to absorber 105. Absorber 105 is designed to allow sulfur compounds, such as hydrogen sulfide ($H_2S$) to come in contact with a chelated metal compound. Hydrogen sulfide may be oxidized to elemental sulfur while the chelated metal compound is reduced. A portion of the elemental sulfur is removed via line 107. The feedstock with reduced hydrogen sulfide content may exit the absorber via line 109. The reduced chelated metal compound and additional elemental sulfur may be sent via line 217 for further separation in sulfur settler vessel 219. Sulfur settler vessel 219 allows for additional separation of solid sulfur from the metal chelate solution. The metal chelate solution may then be sent for regeneration (oxidation) via line 221 to photobioreactor 113. The additional elemental sulfur may be removed from sulfur settler vessel 219 via line 223. Photobioreactor 113 is configured to allow for the bacterial oxidation of the chelated metal compound which when regenerated may be recycled to absorber 105 via line 115. Additionally, the combination of absorber and photobioreactor allows for transport of fixation gases to the photobioreactor where the reduction of the oxidized chelated metal compound allows for carbon or nitrogen fixation. Biomass produced may be removed from photobioreactor 113 via line 117.

Feedstock

The feedstock may be a hydrocarbon stream including sulfur compounds such as hydrogen sulfide (H2S). The hydrocarbon stream may also include other gases, such as carbon dioxide (CO2) and nitrogen (N2), which may be dissolved, entrained, mixed or otherwise included in the hydrocarbon stream. The feedstock may include the hydrocarbon stream, added CO2, and/or added N2. The hydrocarbon stream may include any suitable sulfur containing hydrocarbon stream. Suitable feedstocks from which H2S and CO2 may be removed may include a hydrocarbon stream, such as naturally-occurring gases, synthesis gases, process gases, and/or fuel gases produced by gasification procedures, e.g., gases produced by the gasification of coal, petroleum, shale, tar sands, etc. Hydrocarbon streams, such as coal gasification streams, natural gas streams and refinery feedstocks composed of gaseous hydrocarbon streams, having at least a 2:1 molar ratio of H2S to CO2 may be suitable for use as a feedstock without addition of other gases. The H2S content of the feedstock may vary extensively, but, in general, is typically from about 0.0025 percent to about 10 percent by volume or higher. CO2 content may also vary, and is typically from about 0.1 percent to about 99 percent or greater by volume. The amounts of H2S and CO2 present are not a limiting factor in the processes described, but if the ratio of H2S:CO2 exceeds 2:1, then additional gases may be included in the feedstock to improve process flow and reduce undesired byproducts. For example, if the quantity of H2S exceeds the ratio of H2S:CO2 of about 2:1, then additional CO2 may be added to the feedstock including the use of flue gas and other CO2 sources. Alternatively, if the quantity H2S exceed the ratio of H2S:CO2 of about 2:1, then N2 may be added to the feedstock.

The ratio of H2S to fixation gases allows for the production of elemental sulfur and useful organic carbon and/or nitrogen compounds from acid-gas environments such as from coal or oil hydrogasification or hydroliquefaction processes and natural gas streams. The product of the amine (or other alkaline absorbing solution) stripper used in acid-gas removal processes is suitable as a feedstock for the absorber alone or in combination with other hydrocarbon streams or fixation gases.

Optional Pretreatment

The feedstock may be passed through a pretreatment zone that may include absorbents which are selective to absorbing CO2 (and, in some cases, H2S as well) from the gaseous streams. Suitable absorbents have little or no effect on the activity of the metal chelate, or mixtures of metal chelates. Additionally, absorbents may exhibit sufficient solubility for the reactant or solvents employed. The absorbent may have absorbency for H2S as well, in order to assist in the contacting of H2S present in the gaseous streams with the metal chelates within the absorber. For example, suitable absorbents include diethylene glycol mono ethyl-ether, propylene carbonate, tetraethylene glycol-dimethyl ether, N-methyl pyrrolidone, sulfolane, methyl isobutyl ketone, 2,4-pentanedione, 2,5-hexanedione, diacetone alcohol, hexyl acetate, cyclohexanone, mesityl oxide, and 4-methyl-4-methoxypentone-2 may be used. Suitable temperature and pressure relationships for different CO2-selective absorbents are known or easily calculated. The pretreatment absorbants may at certain pressures and temperatures release CO2 for use in downstream processes including CO2 fixation in the photobioreactor.

Sulfur Oxidation—Absorber

Hydrogen Sulfide may be oxidized to elemental sulfur using metal redox processes, such as solutions including one or more metal chelates. Suitable transition metal chelates and processes for their use are discussed in U.S. Pat. Nos. 4,382,918; 5,126,118; 6,083,472. The oxidation of H2S is coupled to the reduction of a transition metal chelate in a redox reaction. In some embodiments, the metal used is iron and H2S is converted to elemental sulfur and iron reduced according to the following equation:

$$H_2S + 2Fe^{3+} \rightarrow S^0 + 2Fe^{2+} + 2H^+$$

Therefore, the absorption of H2S is typically accomplished in solutions that contain at least the theoretical quantity of metal to provide two moles of metal for each mole of H2S so that the conversion of all or substantially all of the H2S in the feed to sulfur can be carried out in the absorber. While the 2:1 ratio of H2S:metal may not be required (see U.S. Pat. No. 5,126,118), if insufficient oxidized metal is supplied to the absorber, free hydrosulfide and sulfide ions may exist in the solution exiting the absorber and reduce productivity of bacteria in the downstream photobioreactor.

The amount of metal chelate, or mixtures thereof, sufficient to convert all or substantially all of the H2S in the gas stream may be on the order of about two moles or more per mole of H2S. Ratios of metal chelate to H2S may be from about 2:1 to about 15:1, such as about 2:1 to about 10:1, or about 2:1 to about 5:1.

The absorbent including water and the metal chelate can be prepared by any suitable process. For example, the metal chelate may be directly dissolved or suspended in water. The amount of water added may include the amount necessary to achieve dissolution of the metal chelate. A metal chelate solution may be supplied as an aqueous solution having a concentration of from about 0.1 molar to about 3 molar, such as a concentration of about 1 molar. If iron is used, the ligand to iron molar ratio may be from about 1.1 to about 1.6, such as about 1.2 to about 1.4.

Any suitable oxidizing metal chelate may be used, such as metal chelates of iron, copper, nickel, vanadium, cobalt and/or manganese. The metal of the chelate should be capable of oxidizing hydrogen sulfide, while being reduced itself from a higher to a lower oxidation state, and should then be oxidizable by the genetically modified bacteria from the lower oxidation state to the higher oxidation state in a typical redox reaction.

Example reactant materials include coordination complexes in which oxidizing metals form chelates with an acid having the formula:

$$X_{3-n}NY_n$$

where n is a whole number from 1 to 3; Y is an acetic acid or propionic acid group; X is 2-hydroxy ethyl, 2-hydroxy propyl, or an alkyl group having from one to four carbon atoms. Additional suitable metal chelates may be formed by coordination of oxidizing metals with acids having the formula:

$$Y^1Y^2NRNY^3Y^4$$

each of $Y^1$, $Y^2$, $Y^3$, and $Y^4$ are independently selected from acetic and propionic acid groups; from zero to two of $Y^1$, $Y^2$, $Y^3$, and $Y^4$ are independently selected from 2-hydroxy ethyl and 2-hydroxy propyl, and R is ethylene, propylene, or isopropylene or alternatively cyclohexane or benzene where the two hydrogen atoms replaced by nitrogen are in the 1,2 position, and mixtures thereof.

The metal chelates may be formed in aqueous solution by reaction of an appropriate salt, oxide or hydroxide of the metal and the chelating agent in the acid form or an alkali metal or ammonium salt thereof. Exemplary chelating agents include amino acetic acids derived from ammonia or 2-hydroxy alkyl amines, such as glycine, diglycine (imino diacetic acid), NTA (nitrilotriacetic acid), 2-hydroxy alkyl glycine, di-hydroxylalkyl glycine, hydroxyethyl or hydroxypropyl diglycine; amino acetic acids derived from ethylene diamine, diethylene triamine, 1,2-propylene diamine, and 1,3-propylene diamine, such as EDTA (ethylene diamine tetraacetic acid), HEDTA (2-hydroxy ethylethylene diamine triacetic acid), DETPA (diethylene triamine pentaacetic acid), amino acetic acid derivatives of cyclic 1,2-diamines, such as 1,2-diamino cyclohexane-N,N-tetraacetic acid, and 1,2-phenylenediamine-N,N-tetraacetic acid, and amides of polyamino acetic acids (such as those disclosed in Bersworth U.S. Pat. No. 3,580,950). In some embodiments, the iron chelates of NTA and 2-hydroxyethyl ethylene diamine triacetic acid are used.

Sulfur may be recovered by any suitable method, including settling, filtration, liquid flotation, or by suitable devices, such as a hydroclone. It is not necessary that all sulfur be removed on a continuous basis in the process; the process may suitably be operated with a minor inventory or significantly reduced content of sulfur in the system.

The absorber temperature is typically bound by the melting point of the sulfur produced, so that solid sulfur precipitates from the redox reaction mixture. Additionally, if a CO2 adsorbent is used, the temperatures employed in the absorber provide for adequate absorption of CO2. In some commercial applications, such as the removal of H2S and CO2 from natural gas to meet pipeline specifications, absorption at ambient temperatures is typical, since the cost of refrigeration could exceed the benefits obtained due to increased absorption at lower temperatures. In general, the absorber is operated at temperatures from about 10° C. to about 80° C., such as from about 20° C. to about 45° C.

Contact times may be from about 1 second to about 270 seconds or longer, such as a contact time of about 2 seconds to about 120 seconds.

Pressure conditions in the absorber may vary and may depend on the pressure of the gas to be treated. For example, pressures in the absorber may vary from 100 kPa to 20000 kPa, such as from 100 kPa to 10000 kPa. Other conditions of operation for metal chelate sulfur reduction, e.g., pH, etc., are further described in U.S. Pat. Nos. 3,068,065, and 4,009,251, incorporated herein by reference. If the metal chelate is an iron chelate of nitrilotriacetic acid, pH in the absorber may be from about 6 to about 7.5.

The absorber process may include introducing an H2S-containing feedstock and a metal chelate to an absorber. The metal chelate may be introduced as a solution, a solid, or ionic liquid, for example, the metal chelate is introduced as a solution. Additionally, the metal chelate solution may be a regenerated metal chelate from the photobioreactor. The metal chelate is reduced and a solution of reduced metal chelate exits the absorber for biological regeneration through oxidation. The solution of reduced metal chelate typically includes absorbed CO2, which is included in the solution introduced to the photobioreactor. The sulfur produced in the absorber is recovered via separation from the reaction mixture. In some embodiments, the sulfur and metal redox solution exits the absorber and is introduced to an external sulfur settler vessel, where sulfur solids settle and are removed. The removed solid sulfur may contain a small amount of the metal redox solution and be sent to a sulfur recovery apparatus, such as a melter for separating molten sulfur from the metal redox solution. The metal redox solution separated from the settled sulfur is sent to the photobioreactor for regeneration, including oxidation of the metal. Additionally, the absorber process may be conducted continuously.

Metal Oxidation—Photobioreactor

Phototrophic green sulfur bacteria in the photobioreactor accomplish bioconversion of reduced metal chelates and a fixation gas under substantially anaerobic conditions with electromagnetic irradiation being utilized to oxidize metal chelates and reduce carbon dioxide and/or nitrogen. The photosynthetic bioconversion where the metal chelate is an iron chelate and carbon dioxide is the carbon based fixation gas is set forth in the following chemical equation using the photosynthetic sulfur bacteria of the genus *Chlorobium*:

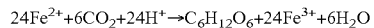

$$24Fe^{2+} + 6CO_2 + 24H^+ \rightarrow C_6H_{12}O_6 + 24Fe^{3+} + 6H_2O$$

Thus, iron is oxidized and carbon dioxide reduced. In the above equation, CO2 is the electron acceptor forming the organic carbon compound. Therefore, from the stoichiometry of the chemical reaction, 4 moles of reduced metal chelate are utilized per mole of carbon dioxide. Any suitable photosynthetic sulfur bacteria can be used, such as bacteria capable of utilizing a reduced metal chelate compound, such as Iron (II) ethylenediaminetetraacetate, as its source of reducing electrons and a carbon or nitrogen source, such as carbon dioxide, as its source of carbon for organic hydrocarbon production (growth). Such photosynthetic sulfur bacteria include those from the genus *Chlorobium*, such as *Chlorobium ferrooxidans* or *Chlorobium tepidum*. The genus and sub-genus may be chosen based on growth rates after genetic modification, if any, as long as the bacteria accept the metal chelate as an electron donor and a carbon or nitrogen source for fixation.

The bioconversion may be performed in a photobioreactor, which may be any suitable anaerobic digestion method, such as a mixed digester, a column in which the bacteria are packed and stabilized so that gas or liquid is passed through the column for a specified detention time, or the bacteria may be arranged in a fixed bed on solid substrates and the reduced metal chelate and carbon or nitrogen source combined stream is passed through the bed. The process could also be performed in a tubular reactor with a continuous flow system or any system in which adequate illumination can be applied. In the photobioreactor, the elemental metal chelate is oxidized by the microorganism during metabolism, and organic carbon or nitrogen is produced. The carbon or nitrogen fixation may produce fixation products that are stored within the microorganism or excreted by the microorganism. Fixation products may include carbon based products such as monosaccharides, polysaccharides, lipids, or biosurfactants. Fixation products may further include nitrogen based products such as ammonia or amino acids. Thus, the products of the bioconversion process are oxidized metal chelate and organically fixed carbon or nitrogen. The biological action being substantially anaerobic provides the advantage that aeration equipment is not required and the chelate solution is more stable (due to the absence of oxygen, which destroys the chelator) The processes described may be carried out by a batch system or by using a continuous reaction system.

The green sulfur bacteria may have improved growth rate under irradiation of certain wavelengths of light. The wavelengths of light that may be used for irradiation of the photosynthetic green sulfur bacteria may include from about 300 nm to about 1200 nm, such as from about 320 nm to about 840 nm (near infrared). However, in some embodiments, the irradiation has a continuous spectral distribution in the wavelengths of from about 300 nm to about 1000 nm, such as from about 320 nm to about 840 nm. Suitable sources for providing the above wavelengths and spectral distribution characteristics may include light-emitting diodes (LEDs), sunlight, tungsten incandescent lamps, halogen-containing tungsten incandescent lamps, xenon discharge lamps, and fluorescent lamps providing line spectra and/or continuous spectra. The density of light utilized is determined on the lower end by the energy required to treat the $H_2S$ obtained and on the high end by photosynthetic efficiency of the system. Typically, the intensity of light is from about 50 micromoles of photons per meter square per second (µmole/m2s) to about 3500 µmole/m2s, such as from about 3250 µmole/m2s to about 3500 µmole/m2s, or from about 3300 µmole/m2s to about 3500 µmole/m2s. In some embodiments, the density of light used is 3500 µmole/m2s. In some embodiments, the light used is white light and is about 3-10 MW*h of light. In other embodiments, red, infrared, or a combination thereof are used and there is less energy expenditure (less than about 10 MW*h). In some embodiments, direct, indirect, or filtered sunlight is used alone or in combination with other light sources. In some embodiments, sunlight is used to supplement LED lighting and reduce the overall cost of providing light for photosynthesis. In some embodiments light is provided continuously and constantly, and in other embodiments light is provided with varying intensity in time, possibly including durations with no light.

The temperature at which the photosynthetic sulfur bacteria exhibit high growth and therefore high oxidation of metal chelates and fixation of carbon and/or nitrogen can be from about 5° C. to about 60° C., such as from about 28° C. to about 50° C. The temperatures of the photobioreactor may be substantially the same as the temperatures of the absorber, meaning that they remain within ±10° C. of the absorber temperature. In some embodiments, the absorber and photobioreactor are run at current ambient temperature. In some embodiments, the light energy introduced to the photobioreactor provides warming of the feeds and effluents such that the photobioreactor is operated at a slightly higher temperature than the absorber, such as about 5° C. greater, or about 10° C. greater than the absorber. The absorber and/or the photobioreactor may allow for cooling, including any suitable cooling method, such as radiant cooling or liquid flow cooling. The absorber and/or the photobioreactor may have internal baffles or fins to improve cooling measures.

The feeds to the photobioreactor may include buffering so as to maintain the pH of the solution within because the photosynthetic green sulfur bacteria exhibit high rates of metabolism in a solution with a pH of about 6 to about 8, such as from about 6.5 to about 7.5, or from about 7 to about 7.3.

Suitable concentrations of the photosynthetic sulfur bacteria in the liquid media are from about 0.5 to about 1.5 grams per liter ash free dry weight (AFDW). Suitable concentrations of metal chelate in the liquid media are from about 0.1 mole percent to about 65 mole percent. In some embodiments, concentrations of less than about 10 to 15 mole percent of the metal chelate in the liquid media may be used to produce high metal chelate oxidation rates. Suitable concentrations of fixation gas in the liquid media are about stoichiometric amounts to 10 to 1000 times excess, as determined based on the concentration of H2S. Ratios of metal chelate to photosynthetic green sulfur bacteria can be from about 0.09 to about 0.16 mole metal chelate per gram of bacteria, such as from about 0.11 to about 0.13 moles of metal chelate per gram photosynthetic green sulfur bacteria. The pressure within the photobioreactor is only bound by the growth rate of the bacteria, for example, a low-pressure process may include pressures from about ambient pressure to about 5 atm pressure. Additionally, a higher-pressure process may include pressures as high as the microorganisms can withstand while maintaining satisfactory metabolism.

The green sulfur bacteria may have a specific growth rate of about 0.04 hr-1 or greater, such as from about 0.1 hr-1, about 0.2 hr-1, or about 0.3 hr-1, to about 0.4 hr-1, or about 0.5 hr-1. In some embodiments, the photobioreactor has a bacterial density of from about 0.5 to about 2 grams AFDW per liter producing a bacterial growth rate of about 0.1 g/L/hr, about 0.2 g/L/hr, about 0.3 g/L/hr, about 0.4 g/L/hr, about 0.5 g/L/hr, about 0.6 g/L/hr, about 0.7 g/L/hr, or about 0.8 g/L/hr, to about 0.5 g/L/hr, about 0.6 g/L/hr, about 0.7 g/L/hr, about 0.8 g/L/hr, about 0.9 g/L/hr, or about 1 g/L/hr.

Bacterial density may be maintained by removal of a portion of the bacteria from the photobioreactor. Removal of bacteria may be accomplished by withdrawal of bacteria cells and liquid medium from the photobioreactor and separation of the cells from the liquid medium. The separation may be accomplished by any suitable means including centrifugation, filtration, or floatation. The liquid medium may be recycled to the photobioreactor or the absorber tower. The excess green sulfur bacteria may include carbon and/or nitrogen sequestered during the course of bacterial growth. The organic carbon compounds may include polysaccharides or lipids and may be used in production of biofuels.

The photobioreactor may also have built in separation to allow the separation of the bacterial culture from the liquid medium including regenerated (oxidized) metal chelate to be returned to the absorber. The photobioreactor may include one or more stages including one or more recycle lines to various portions of the photobioreactor or the absorber.

Genetically Modified Green Sulfur Bacteria

Green sulfur bacteria suitable for genetic modification and use in the photobioreactor include the following genera: Ancalochloris, *Chlorobaculum, Chlorobium*, Clathrochloris, Chloroherpeton, Pelodictyon, and Prosthecochloris. In some embodiments, bacteria of the genus *Chlorobium* are genetically modified (e.g., include cDNA and/or other recombinant DNA) and used in the photobioreactor, such as *Chlorobium ferrooxidans* or *Chlorobium tepidum*.

Chlorosomes, the light-harvesting antenna of green sulfur phototrophic bacteria, are specialized lipoprotein compartments typically including bacteriochlorophyll c, bacteriochorophyll a, carotenoids, and quinones. (Frigaard et al. (2004) J Bacteriol 186,636-53). In wild-type green sulfur bacteria, chlorosomes enable growth under extremely low light conditions. While the use of chlorosomes for light harvesting may be an advantageous survival mechanism, the light harvesting apparatus absorbs enough light to saturate the system even in very low light For photosynthetic bacteria to be used in sulfur removal processes greater efficiency in light use is desired. Therefore, removal of pigmentation of these bacteria may provide a genetically modified strain that has greater efficiency in light use at higher light intensities.

Chlorosomes are mainly made of two components: bacteriochlorophyll c and carotenoids. The chlorosome may be removed or reduced by removal of certain genes from the bacterial genetic code. The chlorosome antenna structure can be eliminated by inactivating the gene that encodes bacteriochlorophyll c synthase protein (bchK gene encodes the BchK protein). Such genetically modified bacteria replicate about 7-fold slower than their wild-type counterparts under low-light conditions, but may not be impaired under higher light intensities. Even with removal of bacteriochlorophyll c, Green Sulfur Bacteria can still perform photosynthesis with the bacteriochlorophyll a in the photosynthetic reaction centers. However, the genetically modified bacteria would likely waste significantly less light under production conditions than the wild-type. The reduction in light wasting will allow the culture to grow to a higher density and have higher productivity (kg H2S oxidized/lhr).

The genetic alteration, a knockout of the bchK gene, changes the composition of chlorosomes to almost exclusively carotenoids. These new structures, termed carotenosomes, are unlikely to function properly as antenna, but the organism may still perform photosynthesis efficiently at both low and high light intensities. If the growth is supported by artificial light, in which the carotenosomes absorb weakly, the genetically modified bacteria may use light efficiently and be suitable for use in the photobioreactor. However, if other sources of light are used it may improve the light use efficiency of the bacteria to also remove carotenoids.

The carotenoids may be removed by deleting the phytoene synthase gene (crtB gene) that encodes the phytoene synthase protein (CrtB protein). The CrtB protein functions in the production of phytoene, a molecule that is a necessary metabolite for the production of carotenoids. The removal of the crtB gene removes carotenoid molecules that absorb in the visible region.

The removal of one or multiple paralogues of the bchK gene and the crtB gene allow for production of genetically modified green sulfur bacteria that are more efficient in light usage, including at high densities.

A bacteriochlorophyll c synthase (bchK) gene may include a nucleotide sequence with at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:1. A bacteriochorophyll c synthase (bchK) gene may include a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, sequence identity (or a range derivable therein) with 150, 200, 250, 300, 350, 400, 450, or 500contiguous base pairs (or a range derivable therein) starting at nucleotide position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 523, 524, 525, 526, 527, 528, 529, 530, 531, 532, 533, 534,535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 6%, 697, 698, 699, 700, 701, 702, 703, 704, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 7%, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 8%, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, or 927 of the nucleotide sequence set forth in SEQ ID NO:1. A bacteriochorophyll c synthase (bchK) gene may or may not have 100% sequence identity with the nucleotide sequence set forth in SEQ ID NO:1. A bacteriochorophyll c synthase (bchK) gene may or may not have 100% sequence identity with 150, 200, 250, 300, 350, 400, 450, or 500 contiguous base pairs of the nucleotide sequence set forth in SEQ ID NO:1. A bacteriochorophyll c synthase (bchK) gene may include a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:1. A bacteriochorophyll c synthase (bchK) gene may encode a protein with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89, 90%, 91%, 92%, 93%, 94%, 95%, 96%, 97%, 98%, 99%, or 100% sequence identity with the amino acid sequence set forth in SEQ ID NO:2.

A phytoene synthase (crtB) gene may include a nucleotide sequence with at least about 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:3. A phytoene synthase (crtB) gene may include a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, sequence identity (or a range derivable therein) with 150, 200, 250, 300, 350, 400, 450, or 500 contiguous base pairs (or a range derivable therein) starting at nucleotide position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 1%, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 2%, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 3%, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, or 783 of the nucleotide sequence set forth in SEQ ID NO:3. A crtB gene may or may not have 100% sequence identity with the nucleotide sequences set forth in SEQ ID NO:3. A phytoene synthase (crtB) gene may or may not have 100% sequence identity with 150, 200, 250, 300, 350, 400, 450, or 500 contiguous base pairs of the nucleotide sequence set forth in SEQ ID NO:3. A crtB gene may include a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:3. A crtB gene may encode a protein with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89, 90%, 91%, 92%, 93%, 94%, 95%, 96%, 97%, 98%, 99%, or 100% sequence identity with the amino acid sequence set forth in SEQ ID NO:4.

In some embodiments, a genetically modified green sulfur bacteria does not include (is a knockout of a gene) bchK and/or crtB.

Additionally, a genetically modified green sulfur bacteria may include a 16S ribosomal RNA sequence with at least about 50%, 52%, 55%, 57%, 60%, 62%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO. 5. A 16s ribosomal RNA sequence may include a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%, sequence identity (or a range derivable therein) with 150, 200, 250, 300, 350, 400, 450, 500, 550, 600, 650, 700, 750, 800, 850, 900, 950, 1000, 1050, 1100, 1150, 1200, 1250, or 1300 contiguous base pairs (or a range derivable therein) starting at nucleotide position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 8%, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, or 1299 of the nucleotide sequence set forth in SEQ ID NO:5. A 16s ribosomal RNA sequence may or may not have 100% sequence identity with the nucleotide sequences set forth in SEQ ID NO:5. A 16s ribosomal RNA sequence may or may not have 100% sequence identity with 150, 200, 250, 300, 350, 400, 450, 500, 550, 600, 650, 700, 750, 800, 850, 900, 950, 1000, 1050, 1100, 1150, 1200, 1250, or 1300 contiguous base pairs of the nucleotide sequence set forth in SEQ ID NO:5. A 16s ribosomal RNA sequence may include a nucleotide sequence with, with at least, or with at most 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity with the nucleotide sequence set forth in SEQ ID NO:5.

Microbe Engineering

A. Overview

Genes and gene products may be introduced into microbial host cells. Suitable host cells for expression of the genes and nucleic acid molecules are microbial hosts that can be found broadly within bacterial families. Examples of suitable host strains include but are not limited to green sulfur bacteria of genera: *Ancalochloris, Chlorobaculum, Chlorobium*, Clathrochloris, *Chloroherpeton, Pelodictyon*, and *Prosthecochloris*.

Vectors or cassettes useful for the transformation of suitable host cells are well known. Typically the vector or cassette contains sequences that direct the transcription and translation of a relevant gene, a selectable marker, and sequences that allow autonomous replication or chromosomal integration. Suitable vectors comprise a region 5' of the gene harboring transcriptional initiation controls and a region 3' of the DNA fragment which controls transcriptional termination. In certain embodiments both control regions are derived from genes homologous to the transformed host cell, although it is to be understood that such control regions need not be derived from the genes native to the specific species chosen as a production host.

Promoters, cDNA, and 3'UTRs, as well as other elements of the vectors, can be generated through cloning techniques using fragments isolated from native sources (see, e.g., Green & Sambrook, Molecular Cloning: A Laboratory Manual, (4th ed., 2012); U.S. Pat. No. 4,683,202 (incorporated by reference)). Alternatively, elements can be generated synthetically using known methods (see, e.g., Gene 164:49-53 (1995)).

B. Homologous Recombination

Homologous recombination is the ability of complementary DNA sequences to align and exchange regions of homology. Transgenic DNA ("donor") containing sequences homologous to the genomic sequences being targeted ("template") is introduced into the organism and then undergoes recombination into the genome at the site of the corresponding homologous genomic sequences.

The ability to carry out homologous recombination in a host organism has many practical implications for what can be carried out at the molecular genetic level and is useful in the generation of a microbe that can produce a desired product. By its nature homologous recombination is a precise gene targeting event and, hence, most transgenic lines generated with the same targeting sequence will be essentially identical in terms of phenotype, necessitating the screening of far fewer transformation events. Homologous recombination also targets gene insertion events into the host chromosome, potentially resulting in excellent genetic stability, even in the absence of genetic selection. Because different chromosomal loci will likely impact gene expression, even from exogenous promoters/UTRs, homologous recombination can be a method of querying loci in an unfamiliar genome environment and to assess the impact of these environments on gene expression.

A particularly useful genetic engineering approach using homologous recombination is to co-opt specific host regulatory elements, such as promoters/UTRs, to drive heterologous gene expression in a highly specific fashion.

Because homologous recombination is a precise gene targeting event, it can be used to precisely modify any nucleotide(s) within a gene or region of interest, so long as sufficient flanking regions have been identified. Therefore, homologous recombination can be used as a means to modify regulatory sequences impacting gene expression of RNA and/or proteins. It can also be used to modify protein coding regions in an effort to modify enzyme activities such as substrate specificity, affinities and Km, thereby affecting a desired change in the metabolism of the host cell. Homologous recombination provides a powerful means to manipulate the host genome resulting in gene targeting, gene conversion, gene deletion, gene duplication, gene inversion, and exchanging gene expression regulatory elements such as promoters, enhancers and 3'UTRs.

Homologous recombination can be achieved by using targeting constructs containing pieces of endogenous sequences to "target" the gene or region of interest within the endogenous host cell genome. Such targeting sequences can either be located 5' of the gene or region of interest, 3' of the gene/region of interest or even flank the gene/region of interest. Such targeting constructs can be transformed into the host cell either as a supercoiled plasmid DNA with additional vector backbone, a PCR product with no vector backbone, or as a linearized molecule. In some cases, it may be advantageous to first expose the homologous sequences within the transgenic DNA (donor DNA) by cutting the transgenic DNA with a restriction enzyme. This step can increase the recombination efficiency and decrease the occurrence of undesired events. Other methods of increasing recombination efficiency include using PCR to generate transforming transgenic DNA containing linear ends homologous to the genomic sequences being targeted.

An additional approach to genetic engineering of bacteria includes chemical mutagenesis. A suitable method for chemical or UV catalyzed mutagenesis is described in multiple publications (Lee et al. (2014) Korean J Chem Eng 31, 1036-1042 and Liu et al. (2015) Appl Biochem and Biotechnol 175, 3507-3518; see also, for example, U.S. Pat. No. 8,232,090; US Patent Application 2012/0088831; US Patent Application 2010/0285557; US Patent Application 2012/0258498).

C. Vectors and Vector Components

Vectors for transforming microorganisms in accordance with the present disclosure can be prepared by known techniques familiar to those skilled in the art in view of the disclosure herein. A vector typically contains one or more genes, in which each gene codes for the expression of a desired product (the gene product) and is operably linked to one or more control sequences that regulate gene expression or target the gene product to a particular location in the recombinant cell.

1. Control Sequences

Control sequences are nucleic acids that regulate the expression of a coding sequence or direct a gene product to a particular location in or outside a cell. Control sequences that regulate expression include, for example, promoters that regulate transcription of a coding sequence and terminators that terminate transcription of a coding sequence. Another control sequence is a 3' untranslated sequence located at the end of a coding sequence that encodes a polyadenylation signal. Control sequences that direct gene products to particular locations include those that encode signal peptides, which direct the protein to which they are attached to a particular location inside or outside the cell.

Thus, an exemplary vector design for expression of a gene in a microbe contains a coding sequence for a desired gene product (for example, a selectable marker, or an enzyme) in operable linkage with a promoter active in yeast. Alternatively, if the vector does not contain a promoter in operable linkage with the coding sequence of interest, the coding sequence can be transformed into the cells such that it becomes operably linked to an endogenous promoter at the point of vector integration.

The promoter used to express a gene can be the promoter naturally linked to that gene or a different promoter.

A promoter can generally be characterized as constitutive or inducible. Constitutive promoters are generally active or function to drive expression at all times (or at certain times in the cell life cycle) at the same level. Inducible promoters, conversely, are active (or rendered inactive) or are significantly up- or down-regulated only in response to a stimulus. Both types of promoters find application in the methods of the present disclosure. Inducible promoters useful in the present disclosure include those that mediate transcription of an operably linked gene in response to a stimulus, such as an exogenously provided small molecule, temperature (heat or cold), lack of nitrogen in culture media, etc. Suitable promoters can activate transcription of an essentially silent gene or upregulate, e.g., substantially, transcription of an operably linked gene that is transcribed at a low level.

Inclusion of termination region control sequence is optional, and if employed, then the choice is primarily one of convenience, as the termination region is relatively interchangeable. The termination region may be native to the transcriptional initiation region (the promoter), may be native to the DNA sequence of interest, or may be obtainable from another source (See, e.g., Chen & Orozco (1988) Nucleic Acids Research 16, 8411).

2. Genes and Codon Optimization

Typically, a gene includes a promoter, a coding sequence, and termination control sequences. When assembled by recombinant DNA technology, a gene may be termed an expression cassette and may be flanked by restriction sites for convenient insertion into a vector that is used to introduce the recombinant gene into a host cell. The expression cassette can be flanked by DNA sequences from the genome or other nucleic acid target to facilitate stable integration of the expression cassette into the genome by homologous recombination. Alternatively, the vector and its expression cassette may remain unintegrated (e.g., an episome), in which case, the vector typically includes an origin of replication, which is capable of providing for replication of the vector DNA.

A common gene present on a vector is a gene that codes for a protein, the expression of which allows the recombinant cell containing the protein to be differentiated from cells that do not express the protein. Such a gene, and its corresponding gene product, is called a selectable marker or selection marker. Any of a wide variety of selectable markers can be employed in a transgene construct useful for transforming the organisms of the present disclosure.

For optimal expression of a recombinant protein, it is beneficial to employ coding sequences that produce mRNA with codons optimally used by the host cell to be transformed. Thus, proper expression of transgenes can require that the codon usage of the transgene matches the specific codon bias of the organism in which the transgene is being expressed. The precise mechanisms underlying this effect are many, but include the proper balancing of available aminoacylated tRNA pools with proteins being synthesized in the cell, coupled with more efficient translation of the transgenic messenger RNA (mRNA) when this need is met. When codon usage in the transgene is not optimized, available tRNA pools are not sufficient to allow for efficient translation of the transgenic mRNA resulting in ribosomal stalling and termination and possible instability of the transgenic mRNA. Resources for codon-optimization of gene sequences are described in (Puigbo et al. (2007) Nucleic Acids Research 35, W126-31), and principles underlying codon optimization strategies are described in (Angov (2011) Biotechnology Journal 6, 650-69). Public databases providing statistics for codon usage by different organisms are available, including at www.kazusaor.jp/codon/and other publicly available databases and resources. D. Transformation Cells can be transformed by any suitable technique including, e.g., biolistics, electroporation, glass bead transformation, and silicon carbide whisker transformation. Any convenient technique for introducing a transgene into a microorganism can be employed in the present disclosure. Transformation can be achieved by, for example, the method of (D. M. Morrison (1979) Methods in Enzymology 68, 326), the method by increasing permeability of recipient cells for DNA with calcium chloride (Mandel & Higa (1970) J. Molecular Biology, 53, 159), or the like.

Examples of expression of transgenes in oleaginous yeast (e.g., *Yarrowia lipolytica*) can be found in the literature (Bordes et al. (2007) J. Microbiological Methods 70 493); Chen et al (1997) Applied Microbiology & Biotechnology 48, 232). Examples of expression of exogenous genes in bacteria such as *E. coli* are well known (Green & Sambrook, Molecular Cloning: A Laboratory Manual, (4th ed., 2012)).

Vectors for transformation of microorganisms in accordance with the present disclosure can be prepared by known techniques familiar to those skilled in the art. In one embodiment, an exemplary vector design for expression of a gene in a microorganism contains a gene encoding an enzyme in operable linkage with a promoter active in the microorganism. Alternatively, if the vector does not contain a promoter in operable linkage with the gene of interest, the gene can be transformed into the cells such that it becomes operably linked to a native promoter at the point of vector integration. The vector can also contain a second gene that encodes a protein. Optionally, one or both gene(s) is/are followed by a 3' untranslated sequence containing a polyadenylation signal. Expression cassettes encoding the two genes can be physically linked in the vector or on separate vectors. Co-transformation of microbes can also be used, in which distinct vector molecules are simultaneously used to transform cells (Protist 155:381-93 (2004)). The transformed cells can be optionally selected based upon the ability to grow in the presence of the antibiotic or other selectable marker under conditions in which cells lacking the resistance cassette would not grow.

Nucleic Acids

A nucleic acid may be inheritable to the progeny of a transformed cell. A gene such as a bchK gene, crtB gene, and/or the lack of such genes may be inheritable because it resides (or is lacking) on a plasmid or chromosome. In certain embodiments, a gene or gene knockout may be inheritable because the gene it is integrated into the genome or the lack gene knockout is not incorporated in the transformed cell.

A gene may comprise conservative substitutions, deletions, and/or insertions while still encoding a protein that has activity. For example, codons may be optimized for a particular host cell, different codons may be substituted for convenience, such as to introduce a restriction site or to create optimal PCR primers, or codons may be substituted for another purpose. Similarly, the nucleotide sequence may be altered to create conservative amino acid substitutions, deletions, and/or insertions.

Proteins may comprise conservative substitutions, deletions, and/or insertions while still maintaining activity. Conservative substitution tables are well known in the art (Creighton, Proteins (2d. ed., 1992)).

Amino acid substitutions, deletions and/or insertions may readily be made using recombinant DNA manipulation techniques. Methods for the manipulation of DNA sequences to produce substitution, insertion or deletion variants of a protein are well known in the art. These methods include M13 mutagenesis, T7-Gen in vitro mutagenesis (USB, Cleveland, Ohio), Quick Change Site Directed mutagenesis (Stratagene, San Diego, Calif.), PCR-mediated site-directed mutagenesis, and other site-directed mutagenesis protocols.

To determine the percent identity of two amino acid sequences or two nucleic acid sequences, the sequences can be aligned for optimal comparison purposes (e.g., gaps can be introduced in one or both of a first and a second amino acid or nucleic acid sequence for optimal alignment and non-identical sequences can be disregarded for comparison purposes). The length of a reference sequence aligned for comparison purposes can be at least 95% of the length of the reference sequence. The amino acid residues or nucleotides at corresponding amino acid positions or nucleotide positions can then be compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. Unless otherwise specified, when percent identity between two amino acid sequences is referred to herein, it refers to the percent identity as determined using the Needleman and Wunsch (J. Molecular Biology 48:444-453 (1970)) algorithm which has been incorporated into the GAP program in the GCG software package (available at http://www.gcg.com), using a Blosum 62 matrix, a gap weight of 10, and a length weight of 4. In some embodiments, the percent identity between two amino acid sequences is determined the Needleman and Wunsch algorithm using a Blosum 62 matrix or a PAM250 matrix, and a gap weight of 16, 14, 12, 10, 8, 6, or 4 and a length weight of 1, 2, 3, 4, 5, or 6. Unless otherwise specified, when percent identity between two nucleotide sequences is referred to herein, it refers to percent identity as determined using the GAP program in the GCG software package (available at http://www.gcg.com), using a NWSgaptina.CMP matrix and a gap weight of 60 and a length weight of 4. In yet another embodiment, the percent identity between two nucleotide sequences can be determined using a gap weight of 40, 50, 60, 70, or 80 and a length weight of 1, 2, 3, 4, 5, or 6. In another embodiment, the percent identity between two amino acid or nucleotide sequences can be determined using the algorithm of E. Meyers and W. Miller (Computer Applications in the Biosciences 4:11-17 (1988)) which has been incorporated into the ALIGN program (version 2.0 or 2.0U), using a PAM120 weight residue table, a gap length penalty of 12 and a gap penalty of 4.

Exemplary computer programs which can be used to determine identity between two sequences include, but are not limited to, the suite of BLAST programs, e.g., BLASTN, MEGABLAST, BLASTX, TBLASTN, TBLASTX, and BLASTP, and Clustal programs, ClustalW, ClustalX, and Clustal Omega.

Sequence searches are typically carried out using the BLASTN program, when evaluating a given nucleic acid sequence relative to nucleic acid sequences in the GenBank DNA Sequences and other public databases. The BLASTX program is effective for searching nucleic acid sequences that have been translated in all reading frames against amino acid sequences in the GenBank Protein Sequences and other public databases.

An alignment of selected sequences in order to determine "% identity" between two or more sequences is performed using for example, the CLUSTAL-W program.

A "coding sequence" or "coding region" refers to a nucleic acid molecule having sequence information necessary to produce a protein product, such as an amino acid or polypeptide, when the sequence is expressed. The coding sequence may comprise and/or consist of untranslated sequences (including introns or 5' or 3' untranslated regions) within translated regions, or may lack such intervening untranslated sequences (e.g., as in cDNA).

The abbreviation used throughout the specification to refer to nucleic acids comprising and/or consisting of nucleotide sequences are the conventional one-letter abbreviations. Thus when included in a nucleic acid, the naturally occurring encoding nucleotides are abbreviated as follows: adenine (A), guanine (G), cytosine (C), thymine (T) and uracil (U). Also, unless otherwise specified, the nucleic acid sequences presented herein is the 5'-3' direction.

As used herein, the term "complementary" and derivatives thereof are used in reference to pairing of nucleic acids by the well-known rules that A pairs with T or U and C pairs with G. Complement can be "partial" or "complete". In partial complement, only some of the nucleic acid bases are matched according to the base pairing rules; while in complete or total complement, all the bases are matched according to the pairing rule. The degree of complement between the nucleic acid strands may have significant effects on the efficiency and strength of hybridization between nucleic acid strands as well known in the art. The efficiency and strength of said hybridization depends upon the detection method.

Any nucleic acid that is referred to herein as having a certain percent sequence identity to a sequence set forth in a SEQ ID NO, includes nucleic acids that have the certain percent sequence identity to the complement of the sequence set forth in the SEQ ID NO.

Carbon Fixation

Four moles of metal chelate are oxidized per mole of CO2 sequestered by the bacteria and two moles of metal chelate are reduced per mole of H2S in the absorber, therefore, the feedstock typically includes twice as much H2S as CO2. When the feedstock is lean on CO2, more fixation gases may be added to at least bring the molar ratio of fixation gas to hydrogen sulfide at or above 1:2. Meaning that for every mole of hydrogen sulfide there should be at least 0.5 moles of fixation gas, such as CO2.

Fixation gases and molecules include carbon dioxide, bicarbonate ion, and dinitrogen gas Fixation gases are not necessarily gases at room temperature, but may also arise from gases in solution, for example, when CO2 is dissolved in mildly basic water the carbonate or bicarbonate anions form. Therefore, bicarbonate and carbonate anions belong in the category of fixation gases. Fixation gases may be included in the hydrocarbon stream that forms the feedstock, or may be added to the hydrocarbon stream in order to form the feedstock. Additionally, fixation gases may be added directly to the absorber or directly to the photobioreactor in addition to or in place of adding fixation gases to the feedstock. Fixation gases may be sourced from the original hydrocarbon stream, flue gas from refinery process, nitrogen removed from air, or other suitable sources.

Likewise, the source of the reductive sulfur compound and the carbon dioxide is not important as long as there is at least the stoichiometric amount of fixation gases, such as one mole of CO2 for two moles of H2S. Typically, the amount of carbon dioxide in the gas stream is in excess of one mole CO2 for 2 moles H2S. In many process effluent streams for which the technology is appropriate, such as acid gas streams or natural gas streams, there is a great excess of CO2 which favors the high removal of small amounts of H2S. When the fixation gas is CO2, the CO2 metabolized by the microorganism forms fixed organic carbon compounds, which may be stored by the microorganism as polysaccharides, lipids or similar organic molecules.

When gas streams having high amounts of H2S are used, CO2 or other fixation gases may be added to provide a stoichiometric excess of fixation gases. For example, the absorber or the feedstock line may allow for introduction of flue gas in order to increase the ratio of CO2 to H2S. Additionally, the fixation gas added does not need to be flue gas, including CO2, but instead may come from any suitable source, such as nitrogen or bicarbonate ion. Whatever the source, the fixation gas should have a minimal oxygen content so as to avoid degradation of the metal chelate or bacteria in question.

The following published resources are incorporated by reference herein for their respective teachings to indicate the level of skill in these relevant arts, and as needed to support a disclosure that teaches how to make and use methods of industrial bio-production of chemical product(s) produced, and also industrial systems that may be used to achieve such conversion with cells of the present disclosure (Biochemical Engineering Fundamentals, 2nd Ed. J. E. Bailey and D. F. Ollis, McGraw Hill, New York, 1986, entire book for purposes indicated and Chapter 9, pages 533-657 in particular for biological reactor design; Unit Operations of Chemical Engineering, 5th Ed., W. L. McCabe et al., McGraw Hill, New York 1993, entire book for purposes indicated, and particularly for process and separation technologies analyses; Equilibrium Staged Separations, P. C. Wankat, Prentice Hall, Englewood Cliffs, N.J. USA, 1988, entire book for separation technologies teachings).

Additives

The absorber and photobioreactor may have other compounds and solvents added to improve reaction rates and stability of reactants. For example, additives for the absorber may include solvents for improved solubility or reaction rates of the metal chelates and hydrogen sulfide. Additionally, additives for the absorber may include stabilizers for the metal chelates, including, pH buffers, excess metal ions, and combination(s) thereof. Additives for the photobioreactor may include fertilizers for bacterial growth, pH buffers, dyes, and combination(s) thereof.

OTHER EMBODIMENTS

The present disclosure provides, among others, the following aspects, each of which may be considered as optionally including alternate aspects.

Clause 1. A process comprising:
introducing a feedstock comprising hydrogen sulfide to an absorber comprising a metal chelate to form a reduced metal chelate; and
introducing the reduced metal chelate to a photobioreactor comprising a phototrophic bacterium.

Clause 2. The process of claim 1, further comprising introducing a fixation gas to one or more of the absorber or the photobioreactor.

Clause 3. The process of claim 2, wherein the feedstock further comprises a fixation gas.

Clause 4. The process of any of claims 2 to 3, further comprising obtaining a fixation product.

Clause 5. The process of any of claims 2 to 4, wherein the fixation gas comprises carbon dioxide, nitrogen, or a combination thereof.

Clause 6. The process of any of claims 4 to 5, wherein the fixation gas comprises carbon dioxide and the fixation product comprises a polysaccharide, lipid or biosurfactant.

Clause 7. The process of any of claims 4 to 5, wherein the fixation gas comprises nitrogen and the fixation product comprises ammonia or amino acids.

Clause 8. The process of any of claims 1 to 7, wherein the phototrophic bacterium is a green sulfur bacterium.

Clause 9. The process of claim 8, wherein the green sulfur bacterium is of the genus *Chlorobium*.

Clause 10. The process of claim 9, wherein the bacterium from the genus *Chlorobium* is *Chlorobium ferrooxidans* and *Chlorobium tepidum*.

Clause 11. The process of any of claims 1 to 9, wherein the bacterium comprises a 16S ribosomal RNA sequence of 80% or greater sequence identity with the nucleotide sequence set forth in SEQ ID NO. 5.

Clause 12. The process of claim 11, wherein the bacterium comprises a 16S ribosomal RNA sequence of 90% or greater sequence identity with the nucleotide sequence set forth in SEQ ID NO. 5.

Clause 13. The process of claim 12, wherein the bacterium comprises a 16S ribosomal RNA sequence of 95% or greater sequence identity with the nucleotide sequence set forth in SEQ ID NO. 5.

Clause 14. The process of any of claims 1 to 13, wherein the bacterium has increased photosynthetic efficiency as compared to wild-type.

Clause 15. The process of any of claims 9 to 14, wherein the bacterium from the genus *Chlorobium* is free of a bacteriochlorophyll c synthase gene, and wherein the bacteriochlorophyll c synthase gene has a 50% or greater sequence identity with the nucleotide sequence set forth in SEQ ID NO:1.

Clause 16. The process in claim 15, wherein the bacteriochlorophyll c synthase gene has a 65% or greater sequence identity with the nucleotide sequence set forth in SEQ ID NO:1.

Clause 17. The process in claim 16, where the bacteriochlorophyll c synthase gene has a 85% or greater sequence identity with the nucleotide sequence set forth in SEQ ID NO:1.

Clause 18. The process in claim 17, where the bacteriochlorophyll c synthase gene has a 95% or greater sequence identity with the nucleotide sequence set forth in SEQ ID NO:1.

Clause 19. The process of any of claims 15 to 18, wherein the bacteriochlorophyll c synthase gene has been removed by the addition of chemical mutagen or UV light.

Clause 20. The process of any of claims 15 to 18, wherein the bacteriochlorophyll c synthase gene has been removed by homologous recombination.

Clause 21. The process of any of claims 9 to 20, wherein the bacteria from the genus *Chlorobium* is free of a Phytoene synthase gene, and wherein the Phytoene synthase gene has a 50% or greater sequence identity with the nucleotide sequence set forth in SEQ ID NO. 3.

Clause 22. The process of claim 21 wherein Phytoene synthase gene has a 65% or greater sequence identity with the nucleotide sequence set forth in SEQ ID NO, 3.

Clause 23. The process of claim 22 wherein Phytoene synthase gene has a 85% or greater sequence identity with the nucleotide sequence set forth in SEQ ID NO. 3.

Clause 24. The process of claim 23 wherein Phytoene synthase gene has a 95% or greater sequence identity with the nucleotide sequence set forth in SEQ ID NO. 3.

Clause 25. An apparatus comprising:
an absorber; and
a photobioreactor fluidly connected to the absorber, the photobioreactor comprising an anaerobic vessel with a light source.

Clause 26. The apparatus of claim 25, wherein the light source comprises filtered or unfiltered sunlight.

Clause 27. The apparatus of claim 25, wherein the light source comprises light emitting diodes and/or sunlight.

Clause 28. The apparatus of any of claims 25 to 27, further comprising a separation unit fluidly connected to the absorber.

Clause 29. The apparatus of claim 28, wherein the separation unit is configured to separate sulfur from the metal chelate.

Clause 30. The apparatus of any of claims 25 to 29, wherein the metal chelate comprises a metal ion selected from the group consisting of iron, copper, cobalt, nickel, manganese, vanadium, and combination(s) thereof.

Clause 31. The apparatus of claim 30, wherein the metal chelate comprises an organic ligand selected from the group consisting of ethylenediaminetetraacetic acid, 2-hydroxyethylethylenediaminetriacetic acid, diethylenetriaminepentaacetic acid, 1,2-diaminocyclohexane-N,N-tetraacetic acid, 1,2-phenylenediamine-N,N-tetraacetic acid, and combination(s) thereof.

Overall, it has been discovered that the combination of metal chelate oxidation of H2S with regeneration using genetically modified green sulfur bacteria can provide an efficient, low cost, sulfur removal system, even for hydrocarbon streams with high sulfur content. Additionally, the processes may include carbon or nitrogen sequestration reducing the output greenhouse gases that may occur in drilling and refining activities. Such processes are amenable to use in proximity to oil and gas wells, and in locations where the cost or size of a Claus plant would otherwise make sulfur reduction and removal infeasible. A hydrocarbon stream including hydrogen sulfide may be used as a direct feed to the absorber. Essentially complete hydrogen sulfide removal is possible thereby eliminating the need for expensive tail gas desulfurization as is necessary with many current hydrogen sulfide removing processes. Additionally, the processes described produce elemental sulfur and useful organic carbon or nitrogen compounds from acid-gas environments such as from coal or oil hydrogasification or hydroliquefaction processes and natural gas streams.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of this disclosure, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, a range includes every point or individual value between its end points even though not explicitly recited. Thus, every point or individual value may serve as its own lower or upper limit combined with any other point or individual value or any other lower or upper limit, to recite a range not explicitly recited.

All documents described herein are incorporated by reference herein, including any priority documents and/or testing procedures to the extent they are not inconsistent with this text. As is apparent from the foregoing general description and the specific embodiments, while forms of this disclosure have been illustrated and described, various modifications can be made without departing from the spirit and scope of this disclosure. Accordingly, it is not intended that this disclosure be limited thereby. Likewise whenever a composition, an element or a group of elements is preceded with the transitional phrase "including," it is understood that we also contemplate the same composition or group of elements with transitional phrases "consisting essentially of," "consisting of," "selected from the group of consisting of," or "is" preceding the recitation of the composition, element, or elements and vice versa. The processes or apparatuses disclosed may be practiced in the absence of any element which is not disclosed herein.

While the present disclosure has been described with respect to a number of embodiments and examples, those skilled in the art, having benefit of this disclosure, will appreciate that other embodiments can be devised which do not depart from the scope and spirit of the present disclosure.

What is claimed is:

1. A process comprising:
   introducing a feedstock comprising hydrogen sulfide to an absorber comprising a metal chelate to form a reduced metal chelate; and
   introducing the reduced metal chelate to a photobioreactor comprising a phototrophic bacterium.

2. The process of claim 1, further comprising introducing a fixation gas to one or more of the absorber or the photobioreactor.

3. The process of claim 1, wherein the feedstock further comprises a fixation gas.

4. The process of claim 1, wherein the feedstock further comprises a fixation gas and further comprising obtaining a fixation product.

5. The process of claim 4, wherein the fixation gas comprises carbon dioxide.

6. The process of claim 4, wherein the fixation gas comprises carbon dioxide and the fixation product comprises a polysaccharide, a lipid, a biosurfactant, or combination(s) thereof.

7. The process of claim 4, wherein the fixation gas comprises nitrogen and the fixation product comprises ammonia, an amino acid, or combination(s) thereof.

8. The process of claim 1, wherein the phototrophic bacterium is a green sulfur bacterium.

9. The process of claim 1, wherein the phototrophic bacterium is a green sulfur bacterium and the green sulfur bacterium is of the genus *Chlorobium*.

10. The process of claim 1, wherein the phototrophic bacterium is a green sulfur bacterium from the genus *Chlorobium* that is *Chlorobium ferrooxidans* or *Chlorobium tepidum*.

11. The process of claim 1, wherein the bacterium comprises a 16S ribosomal RNA sequence of 80% or greater sequence identity with the nucleotide sequence set forth in SEQ ID NO. 5.

12. The process of claim 1, wherein the bacterium comprises a 16S ribosomal RNA sequence of 90% or greater sequence identity with the nucleotide sequence set forth in SEQ ID NO. 5.

13. The process of claim 1, wherein the bacterium comprises a 16S ribosomal RNA sequence of 95% or greater sequence identity with the nucleotide sequence set forth in SEQ ID NO. 5.

14. The process of claim 1, wherein the bacterium is from the genus *Chlorobium* and is free of a bacteriochlorophyll c synthase gene, and wherein the bacteriochlorophyll c synthase gene has a 50% or greater sequence identity with the nucleotide sequence set forth in SEQ ID NO: 1.

15. The process of claim 14, where the bacteriochlorophyll c synthase gene has a 95% or greater sequence identity with the nucleotide sequence set forth in SEQ ID NO: 1.

16. The process of claim 1, wherein the bacteria is from the genus *Chlorobium* and is free of a Phytoene synthase gene, and wherein the Phytoene synthase gene has a 50% or greater sequence identity with the nucleotide sequence set forth in SEQ ID NO. 3.

17. The process of claim 16, wherein the Phytoene synthase gene has a 95% or greater sequence identity with the nucleotide sequence set forth in SEQ ID NO. 3.

* * * * *

SEQUENCE LISTING

```
<160> NUMBER OF SEQ ID NOS: 5

<210> SEQ ID NO 1
<211> LENGTH: 1077
<212> TYPE: DNA
<213> ORGANISM: Chlorobium sp.
<220> FEATURE:
<223> OTHER INFORMATION: bacteriochlorophyll c synthase (bchK)

<400> SEQUENCE: 1
atggtgcgga atatctcctc gccggaggct cacacagtca ttttcaaccg gcccggagcc      60
gttttcacta tctcatcagt catgtcagtt gcaagccaag gattggtcga taaagtaaaa     120
gcccatctcg aactgctcga tcccgtcacc tggatcagcg tttttccttg cctcgccggg     180
ggagtcatgg catccggagc gatgcagccc accgtgcacg actacctgct gctcgcggcg     240 cttttttgc tctacggccc acttggaacc ggctttagcc agtcggtgaa cgactactac       300
gatctcgaac tcgaccgggt caacgagccg acccgcccta ttccgtcggg aaggctgtcg     360
gaaaaagagg caatctggaa ctggagcatc gtgctggtga ttgctgtggc actgagcagc     420
tggatcggca cgagcatcgg cggccagcgc ggcatgattt tcgttggttc gctcctggcc     480
ggccttgtca ttggttatct ctactccgcg cctcctttca agctcaagaa aaacatcttc     540
ttttccgctc cagcggtcgg cttttcctac ggctttatca cctatctttc ggccaatgcg     600
cttttcagcg atattcgccc cgaggtgctc tggcttgccg gacttaattt cttcatggcc     660
gtggcgctca tcgtcatgaa cgacttcaag tcgcaggagg gtgatgccaa agaaggcatg     720
aagtccctga ccgtcatgat tggcgcgaag aacacctttc ttgtcgcctt catcatcatc     780
gacctggtgt tcgccgtctt cgcgtggcgc tcatacatgt gggggttcac gaccctgatg     840
tactttatca ttgcaggact tgtactgaac atcatcattc agattccgat ctatcgcgac     900
```

```
cccaaatcgg gcattacact ggtgcagcac gccgttgacg acggcttcgg caacgctatc      960
ggcaagagcg aggtacagga gcacaacgca ttcctgcggt tccaggtggt taacaacatt     1020
ctgtttctga ccaaccagat gtttgccgcc gcgctgattg gcgcaaagta catgtga       1077
```

<210> SEQ ID NO 2
<211> LENGTH: 358
<212> TYPE: PRT
<213> ORGANISM: Chlorobium sp
<220> FEATURE:
<223> OTHER INFORMATION: bacteriochlorophyll c synthase (bchK)

<400> SEQUENCE: 2

```
Met Val Arg Asn Ile Ser Ser Pro Glu Ala His Thr Val Ile Phe Asn
1               5                   10                  15

Arg Pro Gly Ala Val Phe Thr Ile Ser Ser Val Met Ser Val Ala Ser
            20                  25                  30

Gln Gly Leu Val Asp Lys Val Lys Ala His Leu Glu Leu Leu Asp Pro
        35                  40                  45

Val Thr Trp Ile Ser Val Phe Pro Cys Leu Ala Gly Gly Val Met Ala
    50                  55                  60

Ser Gly Ala Met Gln Pro Thr Val His Asp Tyr Leu Leu Ala Ala
65                  70                  75                  80

Leu Phe Leu Leu Tyr Gly Pro Leu Gly Thr Gly Phe Ser Gln Ser Val
                85                  90                  95

Asn Asp Tyr Tyr Asp Leu Glu Leu Asp Arg Val Asn Glu Pro Thr Arg
            100                 105                 110

Pro Ile Pro Ser Gly Arg Leu Ser Glu Lys Glu Ala Ile Trp Asn Trp
        115                 120                 125

Ser Ile Val Leu Val Ile Ala Val Ala Leu Ser Ser Trp Ile Gly Thr
    130                 135                 140

Ser Ile Gly Gly Gln Arg Gly Met Ile Phe Val Gly Ser Leu Leu Ala
145                 150                 155                 160

Gly Leu Val Ile Gly Tyr Leu Tyr Ser Ala Pro Pro Phe Lys Leu Lys
                165                 170                 175

Lys Asn Ile Phe Phe Ser Ala Pro Ala Val Gly Phe Ser Tyr Gly Phe
            180                 185                 190

Ile Thr Tyr Leu Ser Ala Asn Ala Leu Phe Ser Asp Ile Arg Pro Glu
        195                 200                 205

Val Leu Trp Leu Ala Gly Leu Asn Phe Phe Met Ala Val Ala Leu Ile
    210                 215                 220

Val Met Asn Asp Phe Lys Ser Gln Glu Gly Asp Ala Lys Glu Gly Met
225                 230                 235                 240

Lys Ser Leu Thr Val Met Ile Gly Ala Lys Asn Thr Phe Leu Val Ala
                245                 250                 255

Phe Ile Ile Ile Asp Leu Val Phe Ala Val Phe Ala Trp Arg Ser Tyr
            260                 265                 270

Met Trp Gly Phe Thr Thr Leu Met Tyr Phe Ile Ile Ala Gly Leu Val
        275                 280                 285

Leu Asn Ile Ile Ile Gln Ile Pro Ile Tyr Arg Asp Pro Lys Ser Gly
    290                 295                 300

Ile Thr Leu Val Gln His Ala Val Asp Asp Gly Phe Gly Asn Ala Ile
305                 310                 315                 320

Gly Lys Ser Glu Val Gln Glu His Asn Ala Phe Leu Arg Phe Gln Val
                325                 330                 335
```

```
Val Asn Asn Ile Leu Phe Leu Thr Asn Gln Met Phe Ala Ala Ala Leu
                340                 345                 350

Ile Gly Ala Lys Tyr Met
        355

<210> SEQ ID NO 3
<211> LENGTH: 933
<212> TYPE: DNA
<213> ORGANISM: Chlorobium sp.
<220> FEATURE:
<223> OTHER INFORMATION: phytoene synthase

<400> SEQUENCE: 3
atgaactaca gctataacgg acagacagtg cttcacgacg caggccaaaa gctgtcgctc      60
ccgaacgcct acgactactg ccgccagatc gcccggcacc acgccaagac cttctacctc     120
gccgccaaat tcctgcccaa cgccagcag  aacccgatct ttgccatgta tgccctgttg     180
cgcacggtgg acgacctggt cgatctggcg caggacaagc tgagcaacgg ccagttgaca     240
cgcaaggaga tcaatgactc gattgccgac tggaaaatgc gccttcgcgc ctgttacgat     300
ggctcgccga gcaacgaccc gatcctcatg gcctggcagg ataccctgcg tcactactcg     360
attcccatcg aactgccgct cgacctgatc gacggagtgg cgatggacat cgacttcaag     420
accttcgaga ccttcgacga actctacgtt tactgctaca aggtggcctc ggtagtcggc     480
ctcatgacgg tcgaaatttt cggttacagc aacaaggagg cactccagca cgctatcgac     540
ctcggcatcg ccatgcagct caccaacatc ctgcgcgaca tcggcgagga catcgaccgc     600
aaccgcatct atttgccgct ggaggattta cggcgtttca actacagccg cgaggagttc     660
atgagccgca cgatgaacaa caagttcgtc gatctcatga agttccagat cgatcgcgcc     720
cgaaagtatt acgcctcggc tgaccttggc attccaatgc ttgaaaaaaa cagtcgtctc     780
gccgtcggca tcagcagccg caactacagc gacatcctca aggctatcga agagaacagc     840
tacgatgtct tcacccagcg cgcctaccgc tcgtttttacc agaaactgag caccctgccg     900
tcgatctgga tcaaaaccat gatctcggcc tga                                  933

<210> SEQ ID NO 4
<211> LENGTH: 310
<212> TYPE: PRT
<213> ORGANISM: Chlorobium sp
<220> FEATURE:
<223> OTHER INFORMATION: phytoene synthase

<400> SEQUENCE: 4

Met Asn Tyr Ser Tyr Asn Gly Gln Thr Val Leu His Asp Ala Gly Gln
1               5                   10                  15

Lys Leu Ser Leu Pro Asn Ala Tyr Asp Tyr Cys Arg Gln Ile Ala Arg
            20                  25                  30

His His Ala Lys Thr Phe Tyr Leu Ala Ala Lys Phe Leu Pro Lys Arg
        35                  40                  45

Gln Gln Asn Pro Ile Phe Ala Met Tyr Ala Leu Leu Arg Thr Val Asp
    50                  55                  60

Asp Leu Val Asp Leu Ala Gln Asp Lys Leu Ser Asn Gly Gln Leu Thr
65                  70                  75                  80

Arg Lys Glu Ile Asn Asp Ser Ile Ala Asp Trp Lys Met Arg Leu Arg
                85                  90                  95

Ala Cys Tyr Asp Gly Ser Pro Ser Asn Asp Pro Ile Leu Met Ala Trp
            100                 105                 110
```

Gln Asp Thr Leu Arg His Tyr Ser Ile Pro Ile Glu Leu Pro Leu Asp
            115                 120                 125

Leu Ile Asp Gly Val Ala Met Asp Ile Asp Phe Lys Thr Phe Glu Thr
    130                 135                 140

Phe Asp Glu Leu Tyr Val Tyr Cys Tyr Lys Val Ala Ser Val Val Gly
145                 150                 155                 160

Leu Met Thr Val Glu Ile Phe Gly Tyr Ser Asn Lys Glu Ala Leu Gln
                165                 170                 175

His Ala Ile Asp Leu Gly Ile Ala Met Gln Leu Thr Asn Ile Leu Arg
            180                 185                 190

Asp Ile Gly Glu Asp Ile Asp Arg Asn Arg Ile Tyr Leu Pro Leu Glu
    195                 200                 205

Asp Leu Arg Arg Phe Asn Tyr Ser Arg Glu Glu Phe Met Ser Arg Thr
210                 215                 220

Met Asn Asn Lys Phe Val Asp Leu Met Lys Phe Gln Ile Asp Arg Ala
225                 230                 235                 240

Arg Lys Tyr Tyr Ala Ser Ala Asp Leu Gly Ile Pro Met Leu Glu Lys
                245                 250                 255

Asn Ser Arg Leu Ala Val Gly Ile Ser Ser Arg Asn Tyr Ser Asp Ile
            260                 265                 270

Leu Lys Ala Ile Glu Glu Asn Ser Tyr Asp Val Phe Thr Gln Arg Ala
    275                 280                 285

Tyr Arg Ser Phe Tyr Gln Lys Leu Ser Thr Leu Pro Ser Ile Trp Ile
290                 295                 300

Lys Thr Met Ile Ser Ala
305                 310

<210> SEQ ID NO 5
<211> LENGTH: 1449
<212> TYPE: DNA
<213> ORGANISM: Chlorobium
<220> FEATURE:
<223> OTHER INFORMATION: 16s ribosomal RNA

<400> SEQUENCE: 5
caacggagag tttgatcctg gctcaggacg aacgctggcg gcgtgcctaa cacatgcaag      60
tcaaagtttg agtaacttcg gttacaaaga cttggcgcaa gggtgagtaa ggcataggta     120
atctgccttt tggtctggga taccccgag aaatcgggaa caataccaga tgatgcagcg     180
gaatcgcatg gttatgttgt taaagattta tcgccaaaag atgagcctat gttccatcag     240
gtagttggta gggtaacggc ctaccaagcc tacgacggat agctggtctg agaggatgat     300
cagccacatt ggaactgaga cacggtccag actcctacgg gaggcagcag tgaggaatat     360
tgcgcaatgg gcgaaagcct gacgcagcaa cgccgcgtgg atgatgaagt tcttcggaat     420 gtaaatcct tttgcaggag acgaagaggt cggcttgccg gctgtgacgg taccctgcga     480
ataagccacg gctaactctg tgccagcagc cgcggtgata caggggtggc aagcgttgtc     540
cggatttact gggtgtaaag ggtgcgcagg cggatcgata agtcgggggt taaatccatg     600
tgcttaacac atgcacggct tccgatactg ttgatctaga gtctcgaaga ggaaggtgga     660
atttccggtg taacggtgga atgtgtagat atcggaaaga acaccagtgg cgaaggcagc     720
cttctggtcg agtactgacg ctcaggcacg aaagcgtggg gagcaaacag gattagatac     780
cctggtagtc cacgccgtaa acgatgaata ctagatgttg gtcatagtga tcagtgtcgc     840
agctaacgcg ttaagtattc cacctgggaa gtacgcccgc aagggtgaaa ctcaaaggaa     900

```
                                                -continued ttgacggggg cccgcacaag cggtggatca tgtggtttaa ttcgatgcaa cgcgaagaac    960
cttacctagg cttgatatta cagctaaacc tcctgaaagg gagggtcctt cggggagctg   1020
taacaggtgc tgcatggctg tcgtcagctc gtgtcgtgag atgttgggtt aagtcccgca   1080
acgagcgcaa cccctacaat tagttaccat caggttaagc tggggactct aattgaactg   1140
cctacgcaag tagagaggag ggaggggatg acgtcaagtc ctcatggccc ttacgcctag   1200
ggccacacac gtgatacaat ggcgactaca gagggcaaag ccgcaaggca gagggaatcc   1260
caaaaaagtc gtctcagtcc ggatcggagt ctgcaactcg actccgtgaa gttggaatcg   1320
ctagtaatcg cggatcagca tgccgcggtg aatgtgttcc cgggccttgt acacaccgcc   1380
cgtcaagtca tggaagtcag gagtacccaa agacgctcgc gcgtttaagg taagactggt   1440
aactgggac                                                           1449
```